US008801756B2

(12) United States Patent
Hoy et al.

(10) Patent No.: US 8,801,756 B2
(45) Date of Patent: *Aug. 12, 2014

(54) POLYAXIAL ORTHOPEDIC FASTENING APPARATUS

(75) Inventors: Robert W. Hoy, Paradise, UT (US); T. Wade Fallin, Hyde Park, UT (US); Daniel F. Justin, Logan, UT (US); David W. Meibos, Draper, UT (US)

(73) Assignee: GMEDelaware 2, LLC, Audubon, PA (US)

( * ) Notice: Subject to any disclaimer, the term of this patent is extended or adjusted under 35 U.S.C. 154(b) by 370 days.

This patent is subject to a terminal disclaimer.

(21) Appl. No.: 13/173,776

(22) Filed: Jun. 30, 2011

(65) Prior Publication Data
US 2011/0264143 A1 Oct. 27, 2011

Related U.S. Application Data

(63) Continuation of application No. 11/063,941, filed on Feb. 22, 2005, now Pat. No. 7,993,373, which is a continuation-in-part of application No. 10/860,778, filed on Jun. 2, 2004, now Pat. No. 7,588,590.

(51) Int. Cl.
*A61B 17/70* (2006.01)
(52) U.S. Cl.
USPC ............ 606/247; 606/306; 606/308; 606/310
(58) Field of Classification Search
USPC .................................................. 606/301–321
See application file for complete search history.

(56) References Cited

U.S. PATENT DOCUMENTS

| 5,501,684 | A | * | 3/1996 | Schlapfer et al. ............. 606/301 |
| 5,571,191 | A | * | 11/1996 | Fitz ............................ 623/17.11 |
| 5,613,968 | A | * | 3/1997 | Lin .............................. 606/320 |
| 5,735,851 | A | * | 4/1998 | Errico et al. .................. 606/266 |
| 6,187,005 | B1 | * | 2/2001 | Brace et al. ................... 606/264 |
| 6,835,196 | B2 | * | 12/2004 | Biedermann et al. ......... 606/308 |
| 2004/0006342 | A1 | * | 1/2004 | Altarac et al. ................. 606/61 |
| 2004/0147928 | A1 | * | 7/2004 | Landry et al. .................. 606/61 |
| 2005/0038433 | A1 | * | 2/2005 | Young ............................ 606/61 |
| 2005/0070901 | A1 | * | 3/2005 | David ............................ 606/61 |
| 2006/0149245 | A1 | * | 7/2006 | Sweeney ........................ 606/61 |

\* cited by examiner

*Primary Examiner* — Jerry Cumberledge

(57) ABSTRACT

An orthopedic fastener is designed to attach an implant to bone in such a manner that, until the fastener is tightened, the implant may be rotationally adjusted against the bone. The implant may have a semispherical bone apposition surface that permits polyaxial rotation of the implant against the bone. The orthopedic fastener has an interpositional member and a compression member. The interpositional member may be a split ring with a conical exterior surface that mates with a conical surface of the implant. The compressing member has a threaded bore that engages a proximal end of a fixation member implanted in the bone such that, in response to rotation of the compression member, the interpositional member is sandwiched securely between the implant and the compression member. The conical surface of the implant compresses the interpositional member about a semispherical surface of the compression member, thereby restricting rotation of the implant.

16 Claims, 4 Drawing Sheets

POLYAXIAL ORTHOPEDIC FASTENING APPARATUS

CROSS-REFERENCE TO RELATED APPLICATIONS

This application is a continuation application of U.S. patent application having the Ser. No. 11/063,941 filed on Feb. 22, 2005 which is a continuation-in-part of U.S. application Ser. No. 10/860,778 filed Jun. 2, 2004 which is entitled SPINAL FACET IMPLANT WITH SPHERICAL IMPLANT APPOSITION SURFACE AND BONE BED AND METHODS OF USE, which are incorporated in their entirety herein.

BACKGROUND OF THE INVENTION

1. The Field of the Invention

The present invention relates generally to systems and methods for attaching implants to bone, and more specifically, to a polyaxial orthopedic fastening apparatus particularly useful in the field of facet joint replacement.

2. The Relevant Technology

Orthopedic medicine provides a wide array of implants that can be attached to bone to alleviate various pathologies. One unique challenge in orthopedics is to provide implants and fastening devices that are adaptable to a variety of bone morphologies. Each patient will have a different bone structure; accordingly, it may be necessary to allow for adjustable positioning of an implant with respect to the bone so that the implant will be positioned to perform its function.

For this reason, a number of fixation systems have been invented that enable variation of the angle between the implant and the fastener. Although such fixation systems generally permit adaptation to the bone morphology of a patient to provide secure anchoring of the implant to bone, they are generally somewhat limited in the types of adjustment they permit with respect to the bone. Accordingly, such fixation systems may not be usable with a number of implants that require more comprehensive adjustability. Furthermore, many known implant fixation systems are complex due to the presence of several parts, or due to the need to perform several steps to utilize them to attach an implant to bone. Yet further, some known implant fixation systems are expensive, and require the use of unusual tooling. A need exists in the a for implant fixation systems and methods that alleviate the foregoing shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to anchor orthopedic implants to bone in a manner that provides a high degree of implant adjustability, simplicity, and ease of use. The present invention can be used in any orthopedic procedure, but may have particular utility in the field of facet joint replacement to alleviate back pain resulting from traumatic, inflammatory, metabolic, synovial, neoplastic and degenerative spinal disorders. The configuration and operation of selected embodiments of the invention will be shown and described in greater detail with reference to FIGS. 1 through 4, as follows.

In this application, the terms "compression member" and "interpositional member" are used broadly. A "compression member" generally is a member that receives a compressive force. An "interpositional member" generally is a member, at least part of which is designed to be positioned between at least two other members of a system. Deformation of one part "to lock" another part generally relates to deformation of the first part in such a manner that the first part physically impedes relative motion between the two parts, rather than simply supplying frictional force to provide locking. However, the present invention encompasses embodiments that provide locking solely via one or more frictional forces.

"Polyaxial" rotation is rotation that can occur about at least two axes that are not parallel to each other. "Triaxial rotation" is rotation about three perpendicular axes. Triaxial rotation is equivalent to rotation about a point, because free rotation about any axis of a 3D coordinate system is the same as rotation that is not limited to any axis in the system.

Figure 1:
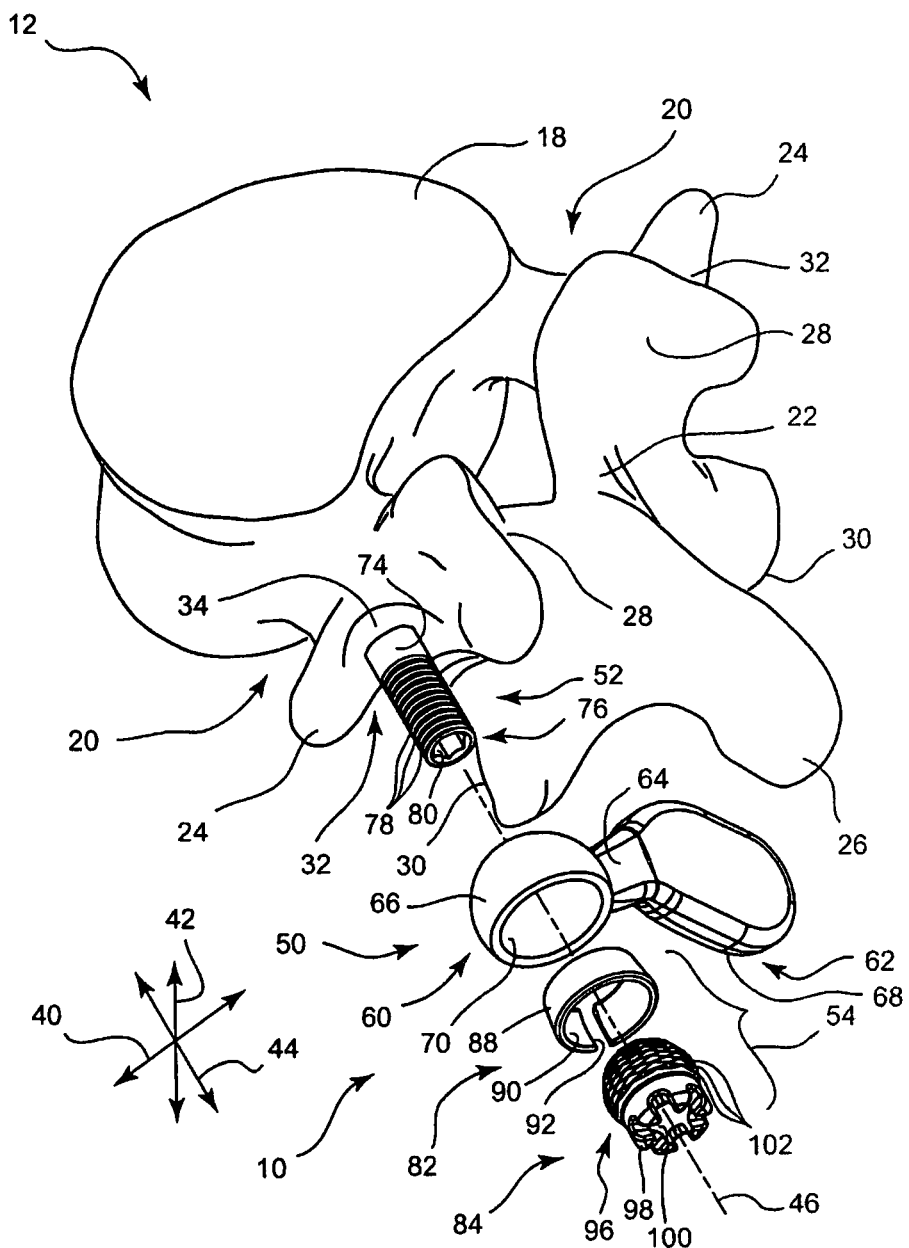
FIG. 1 is an exploded, perspective view of a vertebra with an apparatus according to one embodiment of the invention, with the apparatus positioned for attachment to the vertebra.

Referring to FIG. 1, a perspective view illustrates an apparatus 10 according to one embodiment of the invention, in use with a vertebra 12, such as an L5 lumbar vertebra of a human spine. As shown, the vertebra 12 has a body 18, which is generally disc-shaped. The vertebra 12 also has two pedicles 20 extending from the body 18, and a posterior arch, or lamina 22, that extends between the posterior ends of the pedicles 20 to couple the pedicles 20 together. The vertebra 12 also has a pair of transverse processes 24 that extend laterally from the pedicles 20, and a spinous process 26 that extends posteriorly from the lamina 22.

The vertebra 12 also has a pair of superior facets 28, which are positioned toward the top of the vertebra 12 and face generally medially. Additionally, the vertebra 12 has inferior facets 30, which are positioned toward the bottom of the vertebra 12 and face generally laterally. Each of the pedicles 20 of the vertebra 12 has a saddle point 32, which is positioned generally at the center of the juncture of each superior facet 28 with the adjacent transverse process 24.

The superior facets 28 of the vertebra 12 articulate (i.e., slide and/or press) against the inferior facets (not shown) of an adjacent superior vertebra (not shown) to limit relative motion between the vertebra 12 and the superior vertebra. Thus, the combination of each superior facet 28 with the adjacent inferior facet defines a facet joint (not shown). Accordingly, two facet joints span the distance between each adjacent pair of vertebrae. The inferior facets 30 of the vertebra 30 are part of other facet joints that control motion between the vertebra 12 and ail adjacent inferior vertebra (not shown) and/or the sacrum (also not shown).

Each of the facet joints may be covered by a capsule (not shown) containing a fluid (not shown) that reduces wear of the facets 28, 30 and facilitates articulation. Additionally, layers of cartilage (not shown) may cover the facets 28, 30 to further reduce wear and facilitate articulation. These anatomical structures, as well as the various muscles, ligaments, and nerves of the spine, will not be depicted in the Figures to enhance the clarity of the disclosure. Such structures may be removed or displaced according to known methods to provide the necessary access to the vertebra 12.

As shown, a semispherical resection 34 has been formed on one of the saddle points 32 of the vertebra 12. The semispherical resection 34 is shaped to receive an implant to replace the articular surface of one or both of the adjacent superior and inferior facets 28, 30. The semispherical resection 34 permits relative rotation between the implant and the vertebra 12 about three perpendicular axes prior to fixation of the implant to the vertebra 12. The axes may be defined as shown by reference numerals 40, 42, and 44 in FIG. 1.

More precisely, the axes may include a first axis 40, a second axis 42, and a third axis 44. The first axis 40 is generally collinear with the axis of the corresponding pedicle 20. The second axis 42 is generally vertical (i.e., parallel to the axis of the body 18) and perpendicular to the first axis 40. The third axis 44 is generally horizontal (i.e., parallel to the end plates of the body 18) and perpendicular to the first and second axes 40, 42.

The apparatus 10 includes an implant 50, a fixation member 52, and an orthopedic fastener 54, or fastener 54. The implant 50 is designed to seat against the semispherical resection 34 and to replace the articular surface of the inferior facet 30 immediately inferior to it. Lithe fixation member 52 may take the form of a pedicle screw designed to be implanted in the corresponding pedicle 20 to anchor the implant 50 in place. The orthopedic fastener 54 is designed to be coupled to the fixation member 52 to hold the implant 50 against the vertebral 12.

In the embodiment of FIG. 1, the implant 50 has a fixation portion 60, an articulation portion 62, and a stem 64. The fixation portion 60 is shaped to be attached to the semispherical resection 34, and the articulation portion 62 provides a surface that articulates with an adjacent vertebral facet to carry out the function of the inferior facet 30. The articulation portion 62 is coupled to the fixation portion 60 by the stem 64.

As shown, the fixation portion 60 has a bone apposition surface 66, which may be generally semispherical to correspond to the shape of the semispherical resection 34. The fixation portion 60 also has an aperture (not visible in FIG. 1) that passes through the bone apposition surface 66 to receive the fixation member 52. The aperture is somewhat larger than the exterior surface of the fixation member 52 so that the bone apposition surface 66 is able to slide against the semispherical resection 34 with the fixation member 52 in place, implanted in the pedicle 20.

The articulation portion 62 similarly has an articulation surface 68 designed to articulate with a superior facet of a vertebra immediately inferior to the vertebra 12. The articulation surface 68 may have a convex shape, which may further be semispherical, semicylindrical, or the like. The articulation surface 68 may be designed to articulate with a natural superior facet or a prosthetic superior facet.

In addition to the bone apposition surface, the fixation portion 60 also has an interpositional interface 70 shaped to interact with the fastener 54 in a manner that will be described subsequently. The interpositional interface 70 has a generally conical surface that converges to the aperture of the fixation portion 60.

In the embodiment of FIG. 1, the fixation member 52 has a distal end 74 implanted into one of the pedicles 20 of the vertebra 12, and a proximal end 76 that protrudes from the corresponding saddle point 32. The distal end 74 has threads (not visible in FIG. 1) that facilitate implantation of the distal end 74 in the pedicle 20 and keep the implanted distal end 74 in place. The proximal end 76 has a plurality of threads 78 that are exposed to receive the fastener 54. Additionally, the proximal end 76 has a torquing interface that may be used to apply torque to the fixation member 52 to implant the distal end 74 in the pedicle 20. The torquing interface may take the form of a hexagonal recess into which a hexagonal driver end can be inserted.

As shown in FIG. 1, the fastener 54 includes an interpositional member 82 and a compression member 84. The interpositional member 82 may take the form of a split ring, as illustrated. The compression member 84 is designed to be advanced along the proximal end 76 of the fixation member 52 to press the interpositional member 82 into the interpositional interface 70 of the implant 50.

More specifically, the interpositional member 82 has an implant interface 88, a compression interface 90, and a gap 92. As embodied in FIG. 1, the implant interface 88 includes a generally conical exterior surface designed to mate with the interpositional interface 70 in such a manner that the interpositional member 82 is compressed inward relatively uniformly as it is urged into the interpositional interface 70. The compression interface 90 includes a generally semispherical interior surface designed to receive a corresponding surface of the compression member 84. The gap 92 enables the interpositional member 82 to obtain a relatively high degree of deflection to provide two very distinct configurations: an unlocked configuration, in which the interpositional member 82 is relatively undeflected, and a locked configuration in which the interpositional member 82 is compressed to narrow or remove the gap 92.

The interpositional member 82 may be formed of a material with a relatively low stiffness, such as plastic or rubber. A low stiffness provides relatively high deflection in the interpositional member 82 without requiring excessive force. Accordingly, moving the fastener 54 between the unlocked and locked configurations is relatively easily accomplished.

The compression member 84 has an interpositional interface 96, a torquing interface 98, and a bore 100. The interpositional interface 96 is shaped to mate with the compression interface 90 of the interpositional member 82. More specifically, the interpositional interface 96 may include an exterior, semispherical surface positionable within the compression interface 90. The torquing interface 98 may comprise a castle nut interface, with a plurality of radial projections that can be engaged by the end of a tool (not shown) with projections that mesh with the torquing interface 98. The torquing interface 98 is able to receive torque from such a tool to enable the compression member 84 to be advanced along the proximal end 76 of the fixation member 52.

The bore 100 passes through the compression member 84 and is sized to receive the proximal end 76. The bore 100 has threads (not shown) that engage the threads 78 of the proximal end 76 such that the compression member 84 advances along the proximal end 76 in response to rotation of the compression member 84.

The compression interface 90 and the interpositional interface 96 are sized such that they mate together with clearance when the interpositional member 82 is relatively undeflected. Thus, the interpositional member 82 and the compression member 84 are able to rotate with respect to each other about all three axes 40, 42, 44. Accordingly, when the interpositional member 82 is relatively undeflected or less deflected, the fastener 54 is in an unlocked configuration. When the interpositional member 82 is compressed, the compression interface 90 tightly engages the interpositional interface so that relative rotation about all three axes 40, 42, 44 is restricted. Thus, when the interpositional member 82 is relatively compressed, the fastener 54 is in a locked configuration.

The interpositional interface 96 may have features, such as a plurality of ridges 102, that are designed to engage the interpositional member 82 in the locked configuration to enhance locking. The ridges 102 extend around the circumference of the interpositional interface 96, about the first axis 40. Each of the ridges 102 has a faceted shape, as shown in FIG. 1, so that each ridge 102 has multiple relatively sharp projections that extend outward form the generally semispherical shape of the interpositional interface 96.

The compression member 84 may be formed of a material harder than that of the interpositional member 82. For example, the compression member 84 may be formed of a biocompatible metal. Accordingly, the projections of the ridges 102 may embed themselves into the compression interface 90 when the fastener 54 is moved to the locked configuration to enhance locking by resisting relative rotation between the interpositional member 82 and the compression member 84.

The interpositional interface 96 and the compression interface 90 may be relatively sized such that, in the unlocked configuration, there is little enough clearance that the interpositional member 82 and the compression member 84 will generally remain assembled. Thus, the interpositional member 82 and the compression member 84 may be pre-assembled (i.e., factory assembled or the like), so that the fastener 54 is ready for use at the commencement of the surgical procedure without further assembly.

The fastener 54 may be used in concert with the fixation member 52 to retain the implant 50 in any of a plurality of orientations with respect to the vertebra 12. The manner in which this is carried out will be shown and described in greater detail with reference to FIGS. 2 and 3, as follows.

Figure 2:
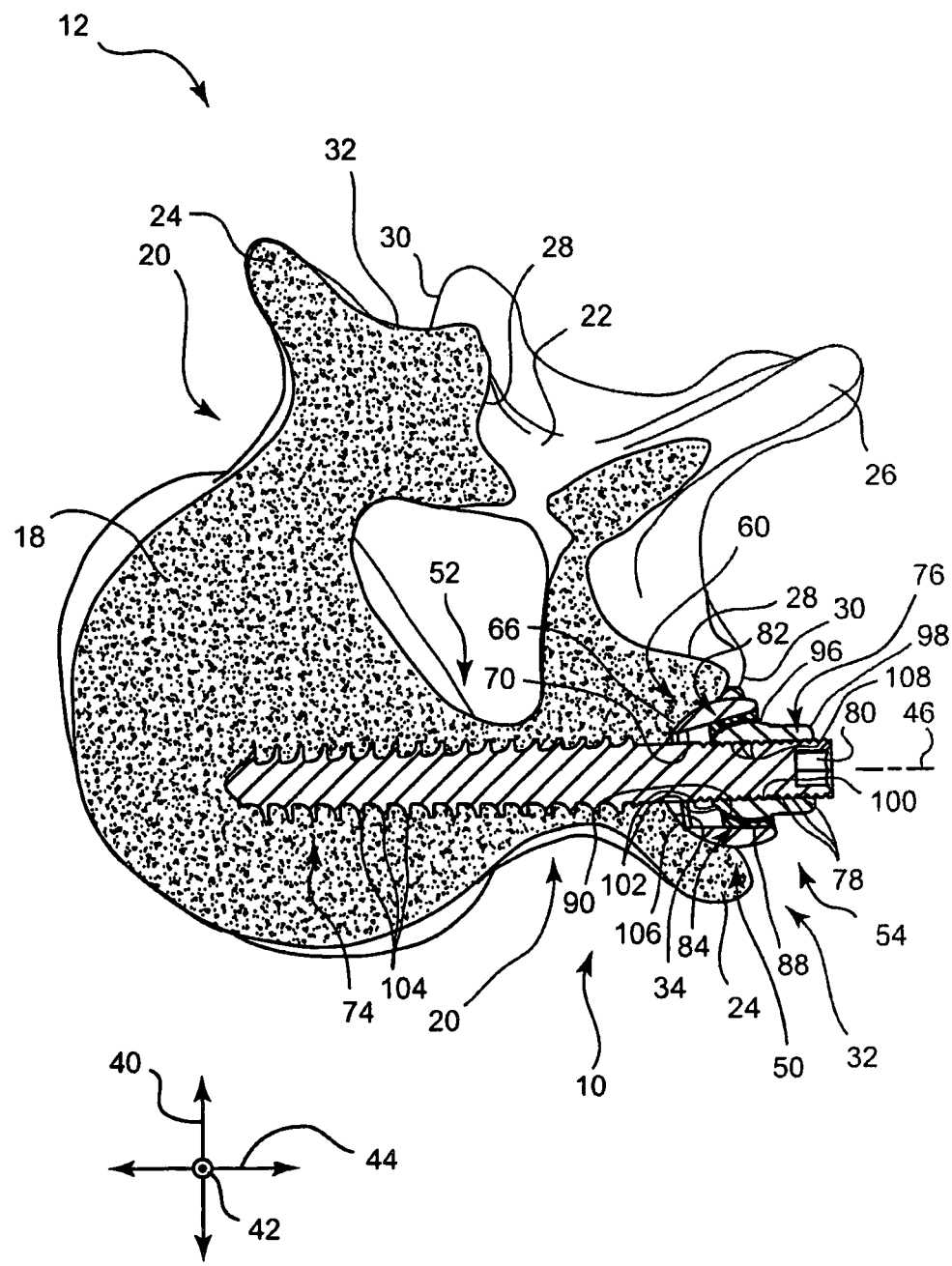
FIG. 2 is a caudal, section view of the vertebra and the apparatus of FIG. 1, with the orthopedic fastener of the apparatus in the unlocked configuration to permit adjustment of the orientation of the implant against the bone.

Referring to FIG. 2, a cephalad, section view illustrates the apparatus 10 and the vertebra 12, with the apparatus 10 fully assembled and with the fastener 54 in the unlocked c: is configuration. As shown, the distal end 74 of the fixation member 52 has threads 104 that are embedded in the body 18 and in the corresponding pedicle 20 of the vertebra 12. The fixation portion 60 of the implant 50 has an aperture 106 to which the generally conical surface of the interpositional interface 70 of the implant 50 converges. The bore 100 of the compression member 84 has threads 108 that engage the threads 78 of the proximal end 76 of the fixation member 52. These elements were briefly described in the discussion of FIG. 1, but were not visible in FIG. 1.

In order to install the implant 50, the posterior elements of the vertebra 12 may first be exposed through the use of procedures known in the art. Measurements may be made to select the implant 50 and determine the appropriate orientation for the implant 50, and any other implants to be installed in the same operation. The semispherical resection 34 may be formed via a reaming operation or the like, and other portions of the vertebra 12, such as the interior facet 30 to be replaced, may be resected as needed. The fixation member 52 may be implanted in the corresponding pedicle 20 along the desired angle.

The implant 50 may then be inserted and positioned such that the bone apposition surface 66 abuts the semispherical resection 34. Prior to adjustment of the orientation of the implant 50, the fastener 54 may be installed so that it can be used to easily fix the implant 50 in place once it has reached the desired orientation. As mentioned previously, the interpositional member 82 and the compression member 84 may be pre-assembled, and therefore, they may not need to be assembled prior to implantation.

The compression member 84, with the interpositional member 82 already coupled to it, may be positioned so that the proximal end 76 of the fixation member 52 passes into the bore 100 of the compression member 84. The compression member 84 may then be rotated to cause the threads 108 of the bore 100 to engage the threads 78 of the proximal end 76. The interpositional member 82 is inserted into the interpositional interface 70 of the implant 50 such that the generally conical implant interface 88 of the interpositional member 82 engages the generally conical surface of the interpositional interface 70. The interpositional member 82' is thereby drawn into coaxiality with the fixation portion 60 of the implant 50.

Further rotation of the compression member 84 will urge the interpositional member 82 further along the interpositional interface 70, toward the pedicle 20. The engagement of the generally conical surfaces of the interpositional interface 70 and the implant interface 88 causes the interpositional member 82 to contract in response to such motion, thereby bringing the fastener 54 to the locked configuration. Until the implant 50 has been adjusted to the desired orientation, the compression member 84 may be rotated just far enough to keep it in place to facilitate subsequent tightening, but not far enough to move the fastener 54 to the locked configuration.

Thus, the apparatus 10 reaches the configuration shown in FIG. 2. The fastener 54 is coupled to the proximal end 76 of the fixation member 52, but has not been tightened. Accordingly, although the orientation of the interpositional member is substantially fixed with respect to the implant 50, the compression member 84 is rotatable about any of the axes 40, 42, 44 with respect to the interpositional member 82. Accordingly, the implant 50 is still relatively freely rotatable about the axes 40, 42, 44 with respect to the vertebra 12.

The implant 50 may then be adjusted by rotating the implant 50 with respect to the vertebra 12 such that the bone apposition surface 66 rotates about any or all of the axes 40, 42, 44 within the semispherical resection 34, until the articulation surface 68 is at the desired position and angle. Then, it is desirable to fix the orientation of the implant 50 with respect to the bone, as will be shown and described in connection with FIG. 3.

Figure 3:
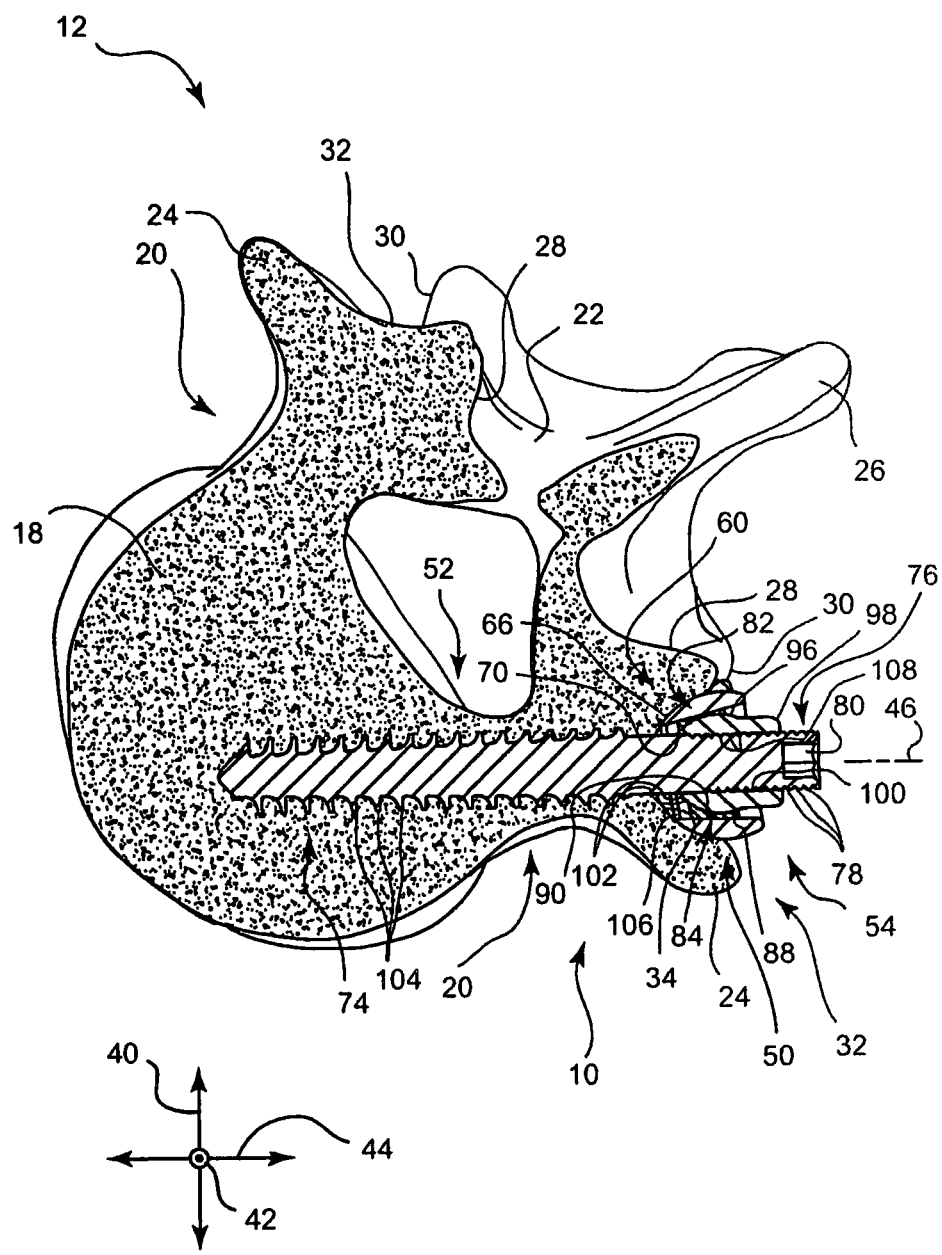
FIG. 3 is a caudal, section view of the vertebra and apparatus of FIG. 1, with the orthopedic fastener in the locked configuration to restrict rotational motion of the implant against the bone.

Referring to FIG. 3, a cephalad, section view illustrates the apparatus 10 and the vertebra 12, with the fastener 54 in the locked configuration. After rotational adjustment of the implant 50 with respect to the vertebra 12, the compression member 84 is further rotated, for example, by engaging the torquing interface 98 with a suitable tool, as described previously, and applying torque. The compression member 84 is advanced along the proximal end 76, toward the pedicle 20 so that the interpositional member 82 is compressed by engagement with the interpositional interface 70 of the implant 50.

As the interpositional member 82 is compressed, the gap 92 shrinks and the compression interface 90 of the interpositional member 82 contracts to grip the interpositional interface 96. The ridges 102, or just the projections thereof, embed themselves in the compression interface 90 to restrict and/or entirely prevent further rotation of the compression member 84 with respect to the interpositional member 82. The interpositional interface 70 of the implant 50 and the implant interface 88 of the interpositional member 82 engage each other in such a manner that relative rotation between the implant 50 and the interpositional member 82 is substantially prevented about the second and third axes 42, 44. Relative rotation about the first axis 40 is also restricted as the interpositional member 82 is compressed, and therefore, provides frictional force as it presses outward against the interpositional interface 70.

Accordingly, when the compression member 84 is advanced along the proximal end 76 to provide the locked configuration, relative rotation between the vertebra 12 and the implant 50 are substantially prevented. This is the configuration illustrated in FIG. 3. The implant 50 is locked in its preferred orientation with respect to the vertebra 12. The implant 50 can be fixed in any of a wide variety of different orientations with respect to the vertebra 12 through the use of the fixation member 52 and the fastener 54.

The embodiment shown in FIGS. 1, 2, and 3 is only one of many embodiments of the present invention. In alternative embodiments, differently shaped implants, interpositional members, compression members, and fixation members may be used. For example, generally conical surfaces need not be used to interface between an implant and an interpositional member. Such an interfacing surface may include cylindrical, semispherical, conical, parabolic, or other shapes, or combinations thereof. According to one alternative embodiment, an interfacing surface man include a cylindrical component adjoining a semicylindrical or parabolic component that flares the interface to provide a diameter larger than that of the cylindrical component. Such an interfacing surface may also have a polygonal cross section, or may be keyed or otherwise shaped to limit an implant to a discrete number of relative orientations with respect to a vertebra.

Similarly, generally semispherical surfaces need not be used to interface between the interpositional member and the compression member. Such interfacing surfaces may include cylindrical, semispherical, conical, parabolic, or other shapes, or combinations thereof. By contrast with the embodiment of FIGS. 1, 2, and 3, alternative embodiments of the invention need not necessarily provide rotation of an implant with respect to a vertebra about three perpendicular axes.

In some alternative embodiments, additional features may be added to enhance locking provided by the locked configuration. Such features may enable an implant to receive greater loads without moving from its preferred orientation with respect to the vertebra. One example of such an alternative embodiment will be shown and described in connection with FIG. 4, as follows.

Figure 4:
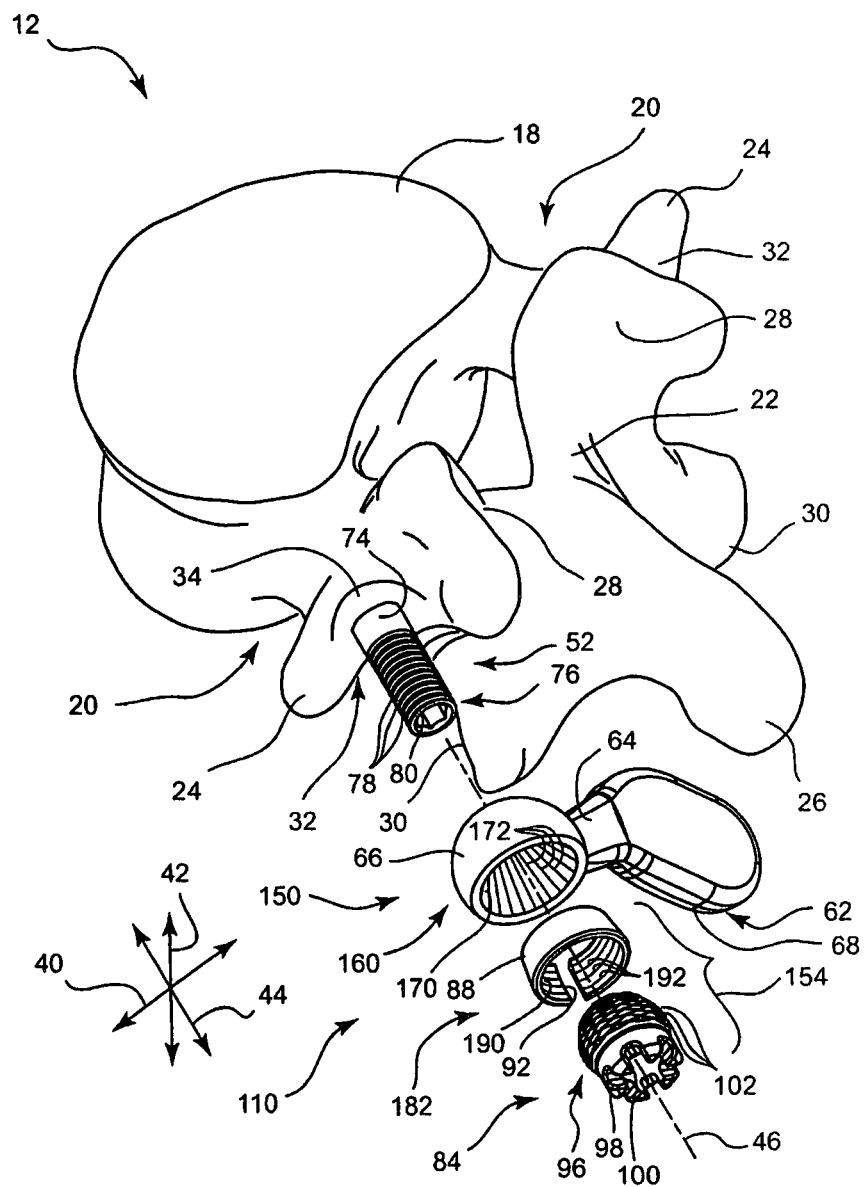
FIG. 4 is an exploded, perspective view of a vertebra with an apparatus according to one alternative embodiment of the invention, with the apparatus positioned for attachment to the vertebra.

Referring to FIG. 4, a perspective view illustrates an apparatus 110 according to one alternative embodiment of the invention, used in conjunction with a vertebra 12, as described previously. As shown, the apparatus 110 includes an implant 150, a fixation member 52, and an orthopedic fastener 154, or fastener 154. The fixation member 52 may be identical to that of the previous embodiment. The implant 150 and the fastener 154 are similar to their counterparts of previous embodiment, but include additional features to enhance locking, as will be described below.

As shown, the implant 150 has a fixation portion 160 designed to be attached to the semispherical resection 34. The fixation portion 160 has an interpositional interface 170, which has a generally conical surface like that of the interpositional interface 70 of the previous embodiment. However, the interpositional interface 170 does not provide a smooth conical surface. Rather, the interpositional interface 170 has a plurality of ridges 172 distributed along a generally radially symmetrical pattern about the generally conical surface.

The ridges 172 protrude inward to resist relative rotation between the implant 150 and an interpositional member 182 of the fastener 154. Like the interpositional member 82 of the previous embodiment, the interpositional member 182 has an implant interface 88 with a generally conical shape. The implant interface mates with the interpositional interface 170 of the implant 150. By contrast with the previous embodiment, the ridges 172 of the interpositional interface 170 are able to penetrate the generally conical surface of the implant interface 88 to restrict, or even substantially prevent, relative rotation between the implant 150 and the interpositional member 182 about the first axis 40.

Penetration of the implant interface 88 by the ridges 172 may occur because the implant 150 may be formed of a material that is harder than that of the interpositional member 182. For example, the interpositional member 182 may be formed of a polymer, elastomer, or the like, while the implant 150 may be formed of a metal, a ceramic, or a harder polymer or elastomer. Thus, the ridges 172 may serve to enhance the locking provided by the locked configuration of the fastener 154.

In addition to the interpositional member 182, the fastener 154 has a compression member 84, which is identical to that of the previous embodiment. However, the interpositional member 182 differs from the interpositional member 82 of the previous embodiment in that the interpositional member 182 has a compression interface 190 with features designed to enhance locking with the interpositional interface 96 of the compression member 84. More precisely, the compression interface 190 includes a generally semispherical surface like that of the previous embodiment. However, the compression interface 190 has a plurality of ridges 192 that extend along generally circular pathways about the circumference of the of the compression interface 190.

In the locked configuration, the ridges 192 enhance locking by helping prevent rotation between the compression interface 190 and the interpositional interface 96 of the compression member 84. More precisely, the ridges 192 may deform against the interpositional interface 96 of the compression member 84, thereby providing regions in which the frictional force between the compression interface 190 and the interpositional interface 96 is relatively large. The ridges 192 may also directly block motion of the ridges 102 of the interpositional interface 96, thereby particularly restricting relative rotation between the interpositional member 182 and the compression member 84 about the second and third axes 42, 44.

Thus, the ridges 172 and the ridges 192 that have been added in the apparatus 110 of FIG. 4 may serve to enhance locking of the orientation of the implant 150 with respect to the vertebra 12, in the locked configuration of the fastener 154. Those of skill in the art will recognize that alternative features may be added to enhance locking. In selected alternatives, the ridges 172 of the interpositional interface 170 of the implant 150 may follow non-converging or curvilinear pathways designed to avoid interfering with compression of the interpositional member 182. Furthermore, the differently-shaped surfaces described previously for interfacing between the implant 50 and the interpositional member 82 or between the interpositional member 82 and the compression member 84 may be used in conjunction with features like the ridges 172 and the ridges 192 of the embodiment of FIG. 4 to provide enhanced locking for such alternative interfacing surface shapes.

The present invention has particular relevance to orthopedic medicine, and more particularly to facet joint replacement. However, the principles, structures, and methods of the present invention may also be extended to a wide variety of other fields. The present invention may be embodied in other specific forms without departing from its spirit or essential characteristics. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An apparatus comprising:
a prosthesis comprising a bone contacting surface comprising a three-dimensional section of a sphere and an articular surface having a generally planar surface shaped to replace a natural articular surface of a bone; and
an orthopedic fastener configured to secure the prosthesis to a bone, the orthopedic fastener comprising:
a compression member comprising a bore defining a first center axis; and
an interpositional member comprising a split ring comprising a flat circular end comprising a center point, and a second center axis extending perpendicular to the flat circular end and through the center point, wherein the interpositional member cooperates with the compression member to provide an unlocked configuration in which the interpositional member is rotatable with respect to the compression member such that the first axis is capable of being selectively oriented to parallel and nonparallel positions relative to the second axis, and a locked configuration in which the second axis is maintained in its selected parallel or nonparallel orientation relative to the first axis and relative rotation between the interpositional member and the compression member is restricted.

2. The apparatus of claim 1, further comprising a fixation member implantable in the bone, the fixation member having a receiving interface configured to cooperate with the compression member to urge the compression member toward the bone.

3. The apparatus of claim 2, wherein the fixation member comprises a distal end shaped to be implanted in the bone, and a proximal end having threads, wherein the compression member comprises threads shaped to cooperate with the threads of the proximal end to cause the compression member to advance toward the distal end in response to rotation of the compression member with respect to the fixation member.

4. The apparatus of claim 1, wherein the bone comprises a vertebra.

5. The apparatus of claim 4, wherein the articular surface is shaped to replace a natural articular surface of a facet of the vertebra.

6. The apparatus of claim 1, wherein the bone contacting surface comprises a generally semispherical shape.

7. The apparatus of claim 1, wherein at least one of the compression member and the interpositional member is configured to deform in response to motion of the compression member toward the bone to lock against the other of the compression member and the interpositional member.

8. The apparatus of claim 7, wherein at least one of the compression member and the interpositional member comprises a plurality of features that protrude toward the other of the compression member and the interpositional member to restrict relative rotation between the compression member and the interpositional member.

9. The apparatus of claim 7, wherein the interpositional member comprises a split ring configured to contract in response to motion of the compression member toward the bone.

10. The apparatus of claim 1, wherein the interpositional member comprises a prosthesis interface having a generally conical shape, wherein the prosthesis comprises an interpositional interface having a generally conical shape that mates with the prosthesis interface to restrict rotation of the prosthesis with respect to the bone about the second axis.

11. The apparatus of claim 10, wherein at least one of the prosthesis interface and the interpositional interface comprises a plurality of features that protrude toward the other of the prosthesis interface and the interpositional interface to restrict relative rotation between the prosthesis and the interpositional member.

12. An apparatus comprising:
a prosthesis comprising an articular surface shaped to replace a natural articular surface of a facet of a vertebra and configured and dimensioned to articulate with a natural articular surface of an adjacent facet;
an orthopedic fastener configured to secure the prosthesis to the vertebra, the orthopedic fastener comprising:
a compression member; and
an interpositional member comprising a locking surface, a prosthesis interface, a flat circular end extending between the locking surface and the prosthesis interface and comprising a center point, and a center axis, wherein the center axis is perpendicular to the flat circular end and passes through the center point, wherein the locking surface engages the compression member to provide an unlocked configuration in which the interpositional member is rotatable with respect to the compression member, and a locked configuration in which relative rotation between the interpositional member and the compression member is restricted, and the prosthesis interface is shaped to engage the prosthesis to press the prosthesis toward the vertebra in response to urging of the compression member toward the vertebra; and
a fixation member implantable in the vertebra, wherein the fixation member is adapted and configured to be selectively oriented to parallel and nonparallel orientations relative to the center axis in the unlocked configuration, and the fixation member is selectively fixed in a parallel or nonparallel orientation relative to the center axis in the locked configuration, the fixation member having a receiving interface configured to cooperate with the compression member to urge the compression member toward the vertebra.

13. The apparatus of claim 12, wherein the fixation member comprises a distal end shaped to be implanted in the vertebra, and a proximal end having threads, wherein the compression member comprises threads shaped to cooperate with the threads of the proximal end to cause the compression member to advance toward the distal end in response to rotation of the compression member with respect to the fixation member.

14. The apparatus of claim 12, wherein at least one of the compression member and the interpositional member is configured to deform in response to motion of the compression member toward the vertebra to lock against the other of the compression member and the interpositional member.

15. The apparatus of claim 14, wherein at least one of the compression member and the interpositional member comprises a plurality of features that protrude toward the other of the compression member and the interpositional member to restrict relative rotation between the compression member and the interpositional member.

16. The apparatus of claim 12, wherein the interpositional member comprises an prosthesis interface having a generally conical shape, wherein the prosthesis comprises an interpositional interface having a generally conical shape that mates with the prosthesis interface to restrict rotation of the prosthesis with respect to the vertebra about the axis.

* * * * *